(12) United States Patent
Schmaling et al.

(10) Patent No.: US 8,578,753 B2
(45) Date of Patent: Nov. 12, 2013

(54) IMPACT TEST FIXTURE WITH SIMULATED CENTRIFUGAL FORCE

(75) Inventors: David N. Schmaling, Southbury, CT (US); Clifford B. Smith, Middletown, CT (US); Eric Lucien Nussenblatt, Norwalk, CT (US)

(73) Assignee: Sikorsky Aircraft Corporation, Stratford, CT (US)

( * ) Notice: Subject to any disclaimer, the term of this patent is extended or adjusted under 35 U.S.C. 154(b) by 351 days.

(21) Appl. No.: 12/968,822

(22) Filed: Dec. 15, 2010

(65) Prior Publication Data

US 2011/0146375 A1    Jun. 23, 2011

Related U.S. Application Data

(60) Provisional application No. 61/287,464, filed on Dec. 17, 2009.

(51) Int. Cl.
| | | |
|---|---|---|
| *G01M 7/00* | (2006.01) | |
| *G01N 3/30* | (2006.01) | |
| *G01N 3/32* | (2006.01) | |
| *G01P 15/00* | (2006.01) | |

(52) U.S. Cl.
USPC .................................... 73/12.01; 73/12

(58) Field of Classification Search
USPC ............................................. 73/12.01, 12
See application file for complete search history.

(56) References Cited

U.S. PATENT DOCUMENTS

| | | | | |
|---|---|---|---|---|
| 4,864,863 A | * | 9/1989 | Yarm ............................ | 73/794 |
| 5,412,996 A | * | 5/1995 | Roberts ........................ | 73/830 |
| 2002/0017144 A1 | * | 2/2002 | Miles et al. ................... | 73/808 |
| 2002/0162400 A1 | * | 11/2002 | Xie et al. ...................... | 73/812 |

FOREIGN PATENT DOCUMENTS

| | | | | |
|---|---|---|---|---|
| JP | 04164231 | | 6/1992 | |
| JP | 04164231 A | * | 6/1992 | ............... G01N 3/32 |
| WO | 2009135136 A2 | | 11/2009 | |
| WO | WO 2009135136 A2 | * | 11/2009 | |

OTHER PUBLICATIONS

European Search Report; Application No. 10195671.2-1236, Sikorsky Aircraft Corporation; European Patent Office, Mar. 15, 2011.

* cited by examiner

*Primary Examiner* — Lisa Caputo
*Assistant Examiner* — Jamel Williams
(74) *Attorney, Agent, or Firm* — Cantor Colburn LLP

(57) ABSTRACT

A test apparatus for a rotor blade of a rotor includes at least one guide rail located in proximity to the rotor blade and at least one bearing secured to the rotor blade radially outboard of the at least one guide rail. The at least one bearing is in operable communication with a radially outboard surface of the at least one guide rail to be translatable thereon. At least one force applicator is in operable communication with the at least one guide rail and is configured to exert a force radially outwardly on the at least one guide rail. The force is transferred to the rotor blade via the at least one bearing and simulates a centrifugal force on the rotor blade. Further disclosed is a method for securing a rotor blade of a rotor in a test fixture.

19 Claims, 4 Drawing Sheets

IMPACT TEST FIXTURE WITH SIMULATED CENTRIFUGAL FORCE

CROSS-REFERENCE TO RELATED APPLICATIONS

This is a nonprovisonal application of U.S. Provisional Application No. 61/287,464, filed on Dec. 17, 2009, the disclosure of which is also incorporated herein by reference.

BACKGROUND OF THE INVENTION

The subject matter disclosed herein relates to impact test fixtures. More specifically, the subject disclosure relates to impact test fixtures for rotating hardware.

Rotating components, for example, helicopter rotor blades, are exposed to impact with birds, shed ice, objects on the ground and the like. Testing performed to demonstrate compliance with impact requirements is typically performed on a rotating blade assembly because the force of the impact on the rotor blades is dependent on the natural frequencies of the blade. These natural frequencies depend on the blade mass and the stiffness of the blade which itself is dependent on centrifugal force generated by the rotating blade. Spinning the rotor blade accurately produces the necessary centrifugal force, but such a test is expensive and properly timing the projectile to impact the desired location on the spinning blade is difficult.

Prior art fixtures have utilized cables, pulleys and/or springs connected to a reinforced portion of the blade which pull the blade radially in an attempt to replicate centrifugal forces in a stationary blade. The reinforcement typically includes a laminate buildup on an outboard section of the blade and a cuff bolted thereto to which the cable or other pulling means would be attached. This configuration adds significant weight to the outboard end of the blade which reduces the natural frequency of the blade resulting in an un-conservative reduction in the force of impact. The art would well-receive improved testing fixtures and methods which would accurately replicate the centrifugal force while reducing the effects of the fixtures on the impact force resulting from the test.

BRIEF DESCRIPTION OF THE INVENTION

According to one aspect of the invention, a test apparatus for a blade of a rotor includes at least one guide rail located in proximity to the rotor blade and at least one bearing secured to the rotor blade radially outboard of the at least one guide rail. The at least one bearing is in operable communication with a radially outboard surface of the at least one guide rail to be translatable thereon. At least one force applicator is in operable communication with the at least one guide rail and is configured to exert a force radially outwardly on the at least one guide rail. The force is transferred to the rotor blade via the at least one bearing and simulates a centrifugal force on the rotor blade.

According to another aspect of the invention, a method for securing a rotor blade of a rotor in a test fixture includes securing a hub of the rotor in a fixed position and locating at least one guide rail in proximity to the rotor blade. At least one bearing is secured to the rotor blade and is in operable communication with a radially outboard surface of the at least one guide rail to be translatable thereon. A radially outwardly directed force is applied to the at least one guide rail, and the force is transferred to the rotor blade via the at least one bearing. The radially outwardly directed force simulates a centrifugal force on the rotor blade.

According to yet another aspect of the invention, a test apparatus for a specimen includes at least one guide rail located in proximity to the specimen and at least one bearing secured to the specimen. The at least one bearing is in operable communication with the at least one guide rail to be translatable thereon. At least one force applicator is configured to exert a force on the at least one guide rail. The force is transferred to the specimen via the at least one bearing, the force simulating an operational force on the specimen.

These and other advantages and features will become more apparent from the following description taken in conjunction with the drawings.

BRIEF DESCRIPTION OF THE DRAWINGS

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

The detailed description explains embodiments of the invention, together with advantages and features, by way of example with reference to the drawings.

DETAILED DESCRIPTION OF THE INVENTION

Figure 1:
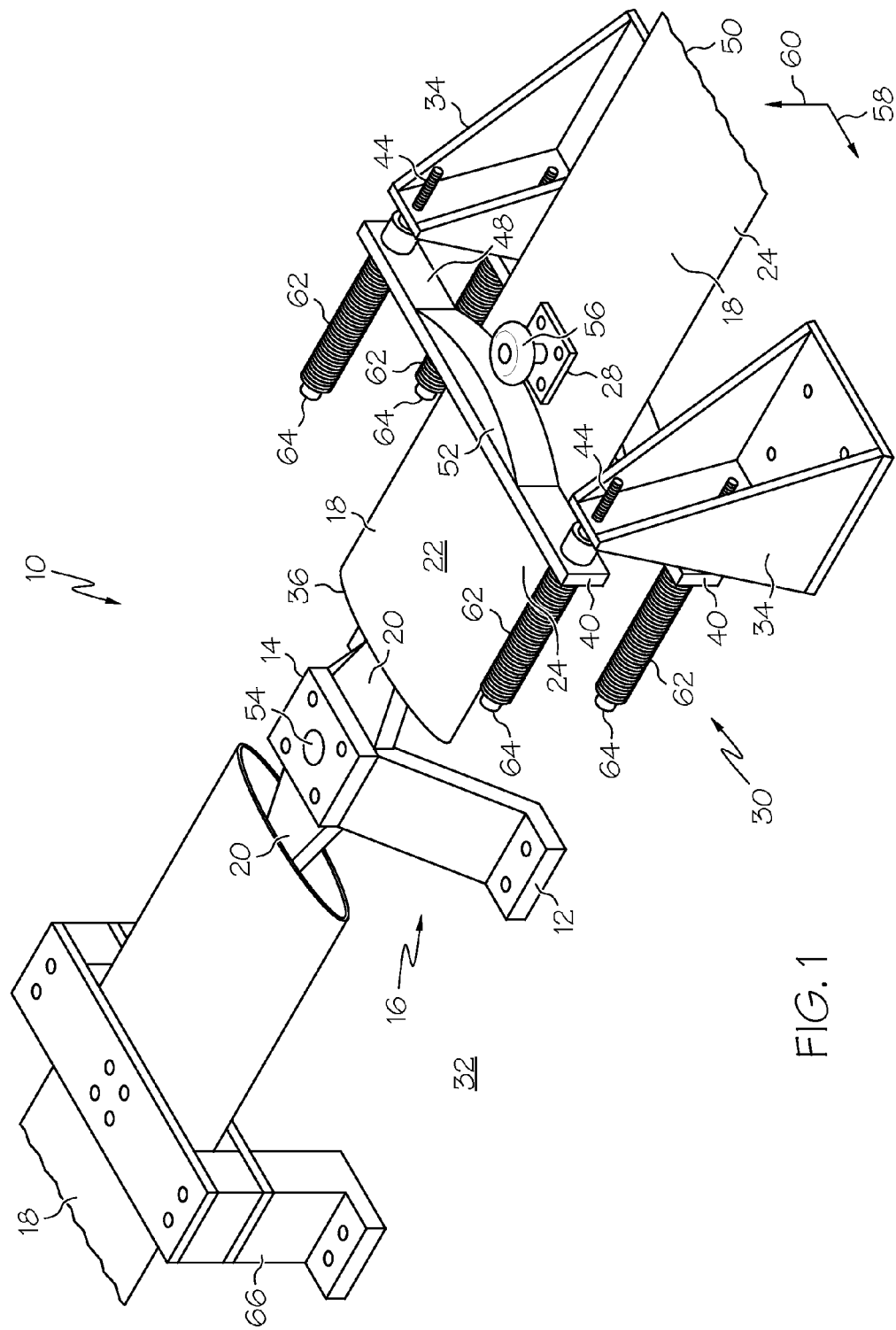
FIG. 1 is a perspective view of an embodiment of a test fixture.

Referring now to FIG. 1, an embodiment of an improved impact test fixture 10 for, for example, helicopter rotor blades, is shown. The test fixture 10 includes a center support 12 to which a hub 14 of a rotor 16 is fixed. The rotor 16 includes a plurality of rotor blades 18 extending radially from the hub 14. In this embodiment, the rotor 16 shown has two rotor blades 18, but it is to be appreciated that rotors 16 having other quantities of rotor blades 18 may be accommodated by the test fixture 10.

Figure 2:
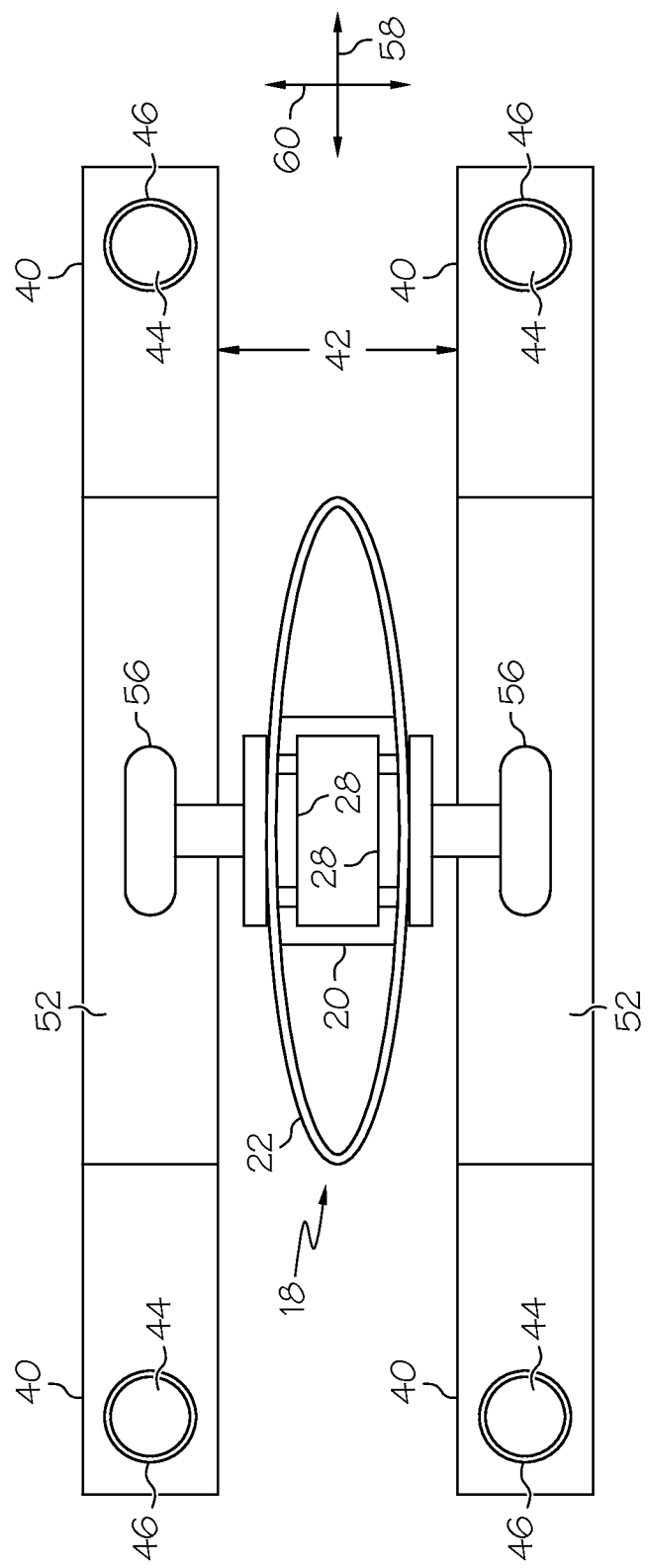
FIG. 2 is partial cross-sectional view of an embodiment of a test fixture.

Referring to FIG. 2, each rotor blade 18 includes a strap 20 extending along a length of the rotor blade 18 which forms an interior support for the blade shell 22 which forms the exterior of the rotor blade 18. The blade shell 22 is formed from, for example, a composite material, while the strap 20 is formed from a metal such as titanium or an alloy thereof. It is to be appreciated, however that the materials described herein are merely exemplary and the use of other materials for the blade shell 22 and/or the strap 20 is contemplated within the scope of the present disclosure. Referring again to FIG. 1, the shell 22 is continuous along a length of the rotor blade 18 and may be secured to the strap 20 along the entire length. In some embodiments, including, for example, bearingless rotors, the shell 22 may be segmented into discrete shell segments 24 which extend partially along a length 26 of the rotor blade 18. Each shell segment 24 includes one or more attachment points 28 along each shell segment 24 to affix the shell segment 24 to the strap 20 by, for example, a plurality of attachment bolts (not shown).

The fixture 10 includes a guide assembly 30 located along the rotor blade 18 to be tested. The guide assembly 30 is located relative to the hub 14 by affixing the guide assembly 30 to, for example, a plate 32, via at least two guide brackets 34. At least one guide bracket 34 is located at each lateral side 36 of the rotor blade 18. Two guide rails 40 extend across the rotor blade 18 between the guide brackets 34 with the rotor blade 18 located in a gap 42 (shown in FIG. 2) between the two guide rails 40. Each guide rail 40 is supported via at least one guide rod 44 extending from each guide bracket 34. In the embodiment of FIG. 1, the guide rods 44 extend parallel to a length of the rotor blade 18. The guide rails 40 include rail holes 46 (shown in FIG. 2) extending therethrough through which the guide rods extend to support the guide rails 40.

Figure 3:
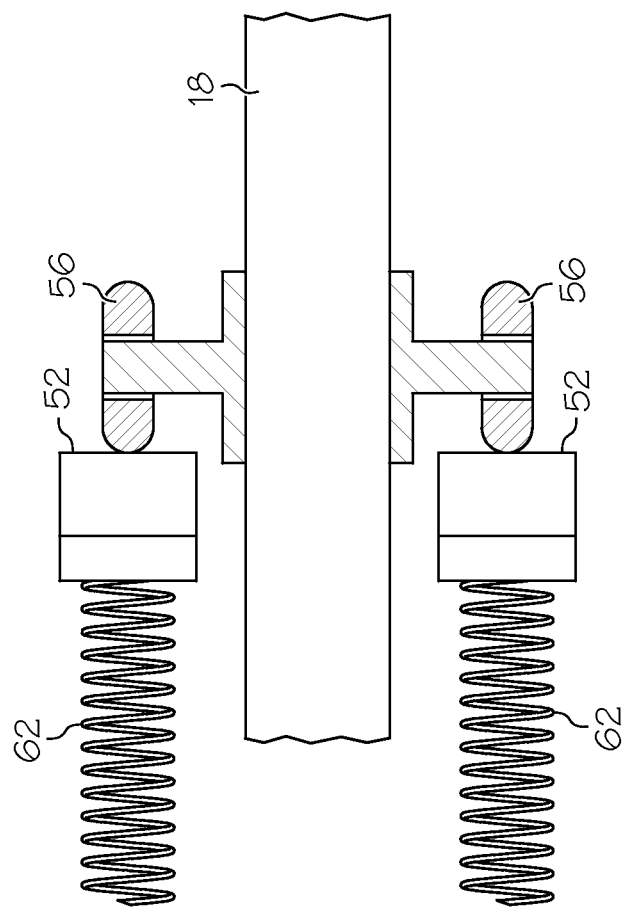
FIG. 3 is another partial cross-sectional view of an embodiment of a test fixture.

An outboard surface 48 of each guide rail 40, located nearest a blade tip 50, includes a curvilinear portion 52 that has a center of curvature 54 at a center of the hub 14. At least one bearing 56 is affixed to the rotor blade 18 such that the bearing abuts the curvilinear portion 52. In some embodiments, as shown in FIG. 3, the two bearings 56 are utilized, one bearing 56 abutting the curvilinear portion 52 of each of the two guide rails 40. The bearing 56 is affixed to the strap 20. In some embodiments, the bearing 56 is affixed to the rotor blade 18 at an existing attachment point 28 utilized to affix the shell segment 24 to the strap 20. In some embodiments, the bearing 56 is located at a center of gravity of the rotor blade 18. Locating the bearing at the center of gravity of the rotor blade 18 allows for more accurate representation of a rotating rotor blade 18 with regard to both loads on and stiffness of the rotor blade 18. Utilizing the attachment point 28 eliminates the need to add additional attachment points/structure to accommodate the bearing 56. Referring again to FIG. 1, the bearing 56 is a low friction bearing and is configured to move along the curvilinear portion 52 in both an in-plane direction 58 and an out-of-plane direction 60 thus allowing movement of the attached rotor blade 18 in the in-plane direction 58 and the out-of-plane direction 60.

To apply a desired simulated centrifugal force to the rotor blade 18, a force is applied to each guide rail 40 in a direction along each guide rod 44 toward the blade tip 50. The force is applied via stacks of Belleville washers 62 which are precompressed and placed on each guide rod 44. The washer 62 stacks are retained on each guide rod 44 by, for example a retaining nut 64. The washer stacks 62 exert a force on the guide rails 40 which is transferred, via the bearings 56, to the rotor blade 18 and acts in a direction toward the blade tip 50. The washer stacks 62 are long to reduce spring rate, and highly compressed to increase the force. In some embodiments, the desired centrifugal force is 12,000 pounds. In some embodiments, alternatives to washer stacks 62 may be utilized to apply the force. For example, a spring (not shown) located at each guide rod 44 may be used.

The opposing rotor blade 18 is fixed to react the force applied to the rotor blade 18 to be tested. This may be accomplished by securing the opposing rotor blade 18 to a retaining bracket 66 which is then fixed to the plate 32. The existing attachment points 28 may be utilized to secure the opposing rotor blade 18 to the retaining bracket. In such embodiments, the opposing rotor blade 18 is first secured to the plate 32 via the retaining bracket 66. The simulated centrifugal force is then applied to rotor blade 18 to be tested by, pulling the rotor blade 18 to be tested away from the opposing rotor blade 18. This is accomplished by assembly the washer stacks 62 to exert a radial force on each guide rail 40 which in turn exerts a radially-directed force on the rotor blade 18 through the bearing 56. Finally, the hub 14 is secured to the plate via a slotted plate attachment (not shown).

Figure 4:
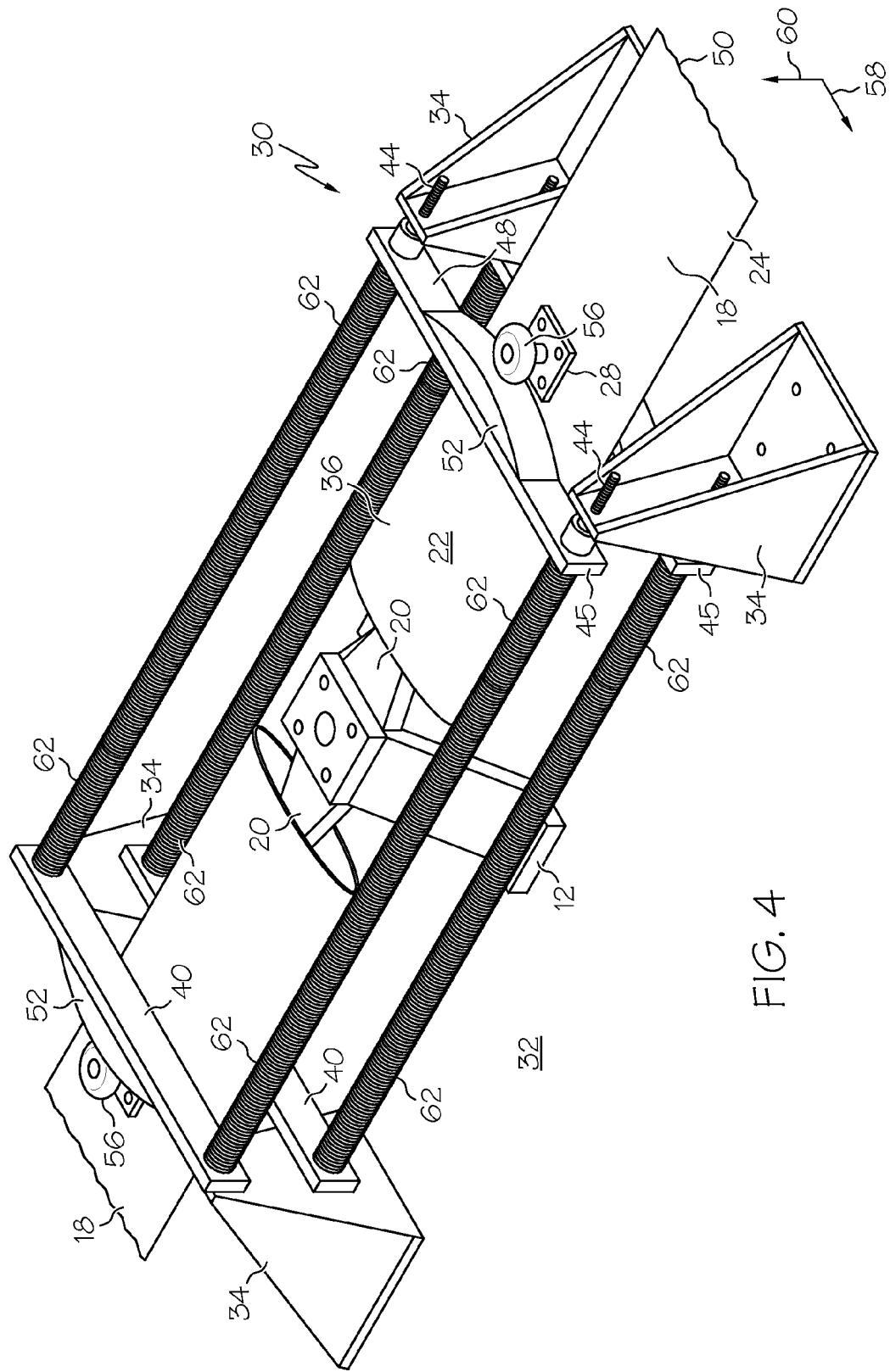
FIG. 4 is a perspective view of another embodiment of a test fixture.

As shown in FIG. 4, in some embodiments, the retaining bracket 66 is not utilized. In these embodiments, a second guide assembly 30 is located at the opposing rotor blade 18, with the same structure as described above. As shown, the guide rods 44 may extend from the first guide assembly 30 to the second guide assembly 30. It is to be appreciated, however, that separate guide rods 44 may be utilized in each guide assembly 30.

During impact testing utilizing the testing fixture 10, the simulated centrifugal force is applied to the rotor blade 18, but because of the configuration of the bearings 56 and the guide rails 40, the rotor blade 18 has freedom of motion, subject to the centrifugal force, in in-plane (lead/lag) and out-of-plane (flap) directions which effectively simulates the motion of a rotating rotor blade 18. The rotor blade 18 is free to react to the impact in virtually any direction. Such movement of the rotor blade 18 is possible due to the fact that the washer stacks 62 are independent allowing skew of the position of each guide rail 40 relative to the rotor blade 18. Further, each guide rail 40 is independent allowing for a change in position of one guide rail 40 relative to the other guide rail 40 in reaction to rotor blade 18 forces from the impact of the projectile during testing. Also, the curvilinear shape of each guide rail 40 maintains the simulated centrifugal force in a direction directly radially outwardly from the center of the hub 14, which is representative of a rotating rotor blade 18. Such a test fixture 10 provides representative impact testing of a stationary rotor blade 18 to eliminate the need for a costly and complex rotating test. By contrast, use of a flat guide rail 40 would result in changes in direction and changes in magnitude of applied force as the rotor blade 18 moves in-plane along the guide rail 40. Further, the use of a curvilinear guide rail 40 has advantages over the cable systems of the prior art in that as the rotor blade moves after impact during testing, the cable would impart an unrealistic restorative force on the rotor blade attempting to recenter the blade.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A test apparatus for a rotor blade of a rotor comprising:
   at least one guide rail disposed in proximity to the rotor blade;
   at least one bearing secured to the rotor blade radially outboard of the at least one guide rail and in operable communication with a radially outboard surface of the at least one guide rail to be translatable thereon; and
   at least one force applicator in operable communication with the at least one guide rail configured to exert a force radially outwardly on the at least one guide rail, the radially outwardly directed force transferred to the rotor blade via the at least one bearing, the force simulating a centrifugal force on the rotor blade.

2. The test apparatus of claim 1 wherein the at least one guide rail is two guide rails.

3. The test apparatus of claim 2 wherein the rotor blade is disposed between the two guide rails.

4. The test apparatus of claim 2 wherein one bearing of the at least one bearing is disposed in operable communication with each guide rail of the two guide rails.

5. A test apparatus for a rotor blade of a rotor comprising:
at least one guide rail disposed in proximity to the rotor blade, wherein a radially outboard surface of the at least one guide rail is curvilinear in shape;
at least one bearing secured to the rotor blade radially outboard of the at least one guide rail and in operable communication with the radially outboard surface of the at least one guide rail to be translatable thereon; and
at least one force applicator in operable communication with the at least one guide rail configured to exert a force radially outwardly on the at least one guide rail, the radially outwardly directed force transferred to the rotor blade via the at least one bearing, the force simulating a centrifugal force on the rotor blade.

6. The test apparatus of claim 5 wherein a center of a radius of curvature of the radially outboard surface is disposed at a central axis of the rotor.

7. The test apparatus of claim 1 wherein two force applicators are disposed in operable communication with each guide rail of the at least one guide rail.

8. The test apparatus of claim 1 wherein the at least one force applicator is a compressed stack of Belleville washers.

9. The test apparatus of claim 1 wherein the at least one bearing is secured to the rotor blade at an attachment point disposed substantially at a center of gravity of the rotor blade.

10. The test apparatus of claim 1 including a retaining bracket secured to an opposing rotor blade to react the force applied to the rotor blade.

11. A method for securing a rotor blade of a rotor in a test fixture comprising:
securing a hub of the rotor in a fixed position;
locating at least one guide rail in proximity to the rotor blade;
securing at least one bearing to the rotor blade and in operable communication with a radially outboard surface of the at least one guide rail to be translatable thereon;
applying a radially outwardly directed force to the at least one guide rail; and
transferring the radially outwardly directed force to the rotor blade via the at least one bearing, the radially outwardly directed force simulating a centrifugal force on the rotor blade.

12. The method of claim 11 comprising locating the rotor blade between two guide rails of the at least one guide rail.

13. The method of claim 12 wherein one bearing of the at least one bearing is disposed in operable communication with each guide rail of the two guide rails.

14. The method of claim 11 wherein the at least one bearing is translatable on a curvilinear portion of the radially outboard surface of each guide rail.

15. The method of claim 14 wherein a center of a radius of curvature of the curvilinear portion is disposed at a central axis of the rotor.

16. The method of claim 11 wherein the radially outward force is applied via two force applicators disposed in operable communication with each guide rail of the at least one guide rail.

17. The method of claim 16 wherein each force applicator is a compressed stack of Belleville washers.

18. The method of claim 11 comprising securing the at least one bearing to the rotor blade at an attachment point disposed substantially at a center of gravity of the rotor blade.

19. The method of claim 11 including retaining an opposing rotor blade of the rotor to react the force applied to the rotor blade.

* * * * *